United States Patent
Wang et al.

(10) Patent No.: US 9,249,078 B2
(45) Date of Patent: Feb. 2, 2016

(54) MIXED METAL OXIDE CATALYSTS AND USE THEREOF

(75) Inventors: Kun Wang, Bridgewater, NJ (US); Roberto Garcia, Easton, PA (US); Charles Morris Smith, Princeton, NJ (US); Doron Levin, Highland Park, NJ (US); James C. Vartuli, Bradenton, FL (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/347,422

(22) PCT Filed: Aug. 29, 2012

(86) PCT No.: PCT/US2012/052878
§ 371 (c)(1),
(2), (4) Date: Jul. 21, 2014

(87) PCT Pub. No.: WO2013/052217
PCT Pub. Date: Apr. 11, 2013

(65) Prior Publication Data
US 2015/0148567 A1   May 28, 2015

Related U.S. Application Data

(60) Provisional application No. 61/544,341, filed on Oct. 7, 2011.

(51) Int. Cl.
| | | |
|---|---|---|
| *C07C 37/08* | (2006.01) | |
| *C07C 407/00* | (2006.01) | |
| *C07C 2/66* | (2006.01) | |
| *C07C 45/53* | (2006.01) | |
| *B01J 21/06* | (2006.01) | |
| *B01J 37/03* | (2006.01) | |
| *B01J 37/06* | (2006.01) | |
| *B01J 23/00* | (2006.01) | |
| *B01J 23/30* | (2006.01) | |
| *B01J 37/00* | (2006.01) | |
| *B01J 23/10* | (2006.01) | |

(52) U.S. Cl.
CPC ............ *C07C 37/08* (2013.01); *B01J 21/066* (2013.01); *B01J 23/002* (2013.01); *B01J 23/10* (2013.01); *B01J 23/30* (2013.01); *B01J 37/009* (2013.01); *B01J 37/036* (2013.01); *B01J 37/06* (2013.01); *C07C 2/66* (2013.01); *C07C 45/53* (2013.01); *C07C 407/00* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 3,821,314 A | 6/1974 | Arkell et al. | |
| 3,959,381 A | 5/1976 | Arkell et al. | |
| 4,021,490 A | 5/1977 | Hudson | |
| 4,230,638 A | 10/1980 | Murtha | |
| 4,262,151 A | 4/1981 | Pujado | |
| 4,358,618 A | 11/1982 | Sifniades et al. | |
| 4,480,141 A | 10/1984 | Drake | |
| 4,482,757 A | 11/1984 | Drake | |
| 4,487,970 A | 12/1984 | Drake | |
| 4,490,565 A | 12/1984 | Chang et al. | |
| 4,490,566 A | 12/1984 | Chang et al. | |
| 4,870,217 A | 9/1989 | Knifton | |
| 4,898,995 A | 2/1990 | Knifton et al. | |
| 5,254,751 A | 10/1993 | Zakoshansky | |
| 5,345,026 A | 9/1994 | Chang et al. | |
| 5,383,731 A | 1/1995 | Hattori et al. | |
| 5,780,382 A | 7/1998 | Chang et al. | |
| 5,854,170 A | 12/1998 | Chang et al. | |
| 6,037,513 A | 3/2000 | Chang et al. | |
| 6,124,232 A | 9/2000 | Chang et al. | |
| 6,162,757 A | 12/2000 | Chang et al. | |
| 6,169,215 B1 | 1/2001 | Levin et al. | |
| 6,284,927 B1 | 9/2001 | Druliner et al. | |
| 6,297,406 B1 * | 10/2001 | Levin et al. | 568/798 |
| 6,720,462 B2 | 4/2004 | Kuhnle et al. | |
| 6,852,893 B2 | 2/2005 | Kuhnle et al. | |
| 7,102,037 B2 * | 9/2006 | Levin et al. | 568/908 |
| 7,399,891 B2 * | 7/2008 | Yarbrough et al. | 568/908 |
| 7,597,865 B2 * | 10/2009 | Mori et al. | 423/213.2 |
| 2003/0083527 A1 | 5/2003 | Kuhnle et al. | |

(Continued)

FOREIGN PATENT DOCUMENTS

| | | |
|---|---|---|
| CN | 101560396 | 7/2012 |
| EP | 2 072 120 | 6/2009 |

(Continued)

OTHER PUBLICATIONS

U.S. Appl. No. 61/544,341, filed Oct. 7, 2011, Wang et al.

(Continued)

*Primary Examiner* — Brian J Davis
(74) *Attorney, Agent, or Firm* — Stephen Baehl

(57) ABSTRACT

Disclosed herein are catalyst compositions useful in selective decomposition of organic oxygenates. A feed comprising an organic oxygenate may be contacted with a catalyst comprising (a) at least 0.1 wt % of an oxide of an element selected from Group 3 of the Periodic Table of Elements, wherein Group 3 includes the Lanthanide series; (b) at least 0.1 wt % of an oxide of an element selected from Group 6 of the Periodic Table of Elements; and (c) at least 0.1 wt % of an oxide of at least one element selected from Group 4 of the Periodic Table of Elements, wherein the wt % s are based upon the total combined weight of the oxides in (a) through (c) and excludes any other components.

17 Claims, 3 Drawing Sheets

(56) References Cited

U.S. PATENT DOCUMENTS

| | | | |
|---|---|---|---|
| 2004/0162446 A1 | 8/2004 | Black | |
| 2004/0236152 A1 | 11/2004 | Black et al. | |
| 2007/0265476 A1 | 11/2007 | Dakka et al. | |
| 2008/0095682 A1* | 4/2008 | Kharas et al. | 423/239.1 |
| 2010/0111793 A1* | 5/2010 | Mori et al. | 423/239.1 |
| 2010/0197978 A1* | 8/2010 | Dakka et al. | 568/900 |
| 2011/0190546 A1 | 8/2011 | Dakka et al. | |

FOREIGN PATENT DOCUMENTS

| | | |
|---|---|---|
| GB | 681613 | 11/1950 |
| GB | 0 492 807 | 7/1992 |
| JP | 2007-099745 | 4/2007 |
| JP | 2007-099746 | 4/2007 |
| WO | WO 2005/066101 | 7/2005 |
| WO | 2006/015826 | 2/2006 |
| WO | 2008/128638 | 10/2008 |
| WO | 2009/025939 | 2/2009 |
| WO | 2009/058527 | 5/2009 |
| WO | WO 2009/131769 | 10/2009 |
| WO | WO 2010/042261 | 4/2010 |
| WO | WO 2010/098916 | 9/2010 |
| WO | 2011/001244 | 1/2011 |
| WO | 2011/031374 | 3/2011 |

OTHER PUBLICATIONS

Leitenburg et al., "*A Novel and Simple Route to Catalysts with a High Oxygen Storage Capacity: the Direct Room-temperature Synthesis of $CeO_2$-$ZrO_2$ Solid Solutions*", J. Chem. Soc., Chem. Commun., 1995, pp. 2181-2182.

Meriani, S., "*Features of the Caeria-Zirconia System*", Materials Science and Engineering: A, vol. 109, Mar. 1989, pp. 121-130.

Trovarelli, A. "*Catalytic Properties of Ceria and $CeO_2$-Containing Materials*", Catalysis Reviews: Science and Engineering, vol. 38, Issue 4, 1996, pp. 440-520.

Corma et al., "*Discovery of New Paraffin Isomerization Catalysts Based On $SO_4^{2-}$-$/ZrO_2$ and $WO_x/ZrO_2$ Applying Combinatorial Techniques*", Catalysis Today, vol. 81, Issue 3, Jun. 30, 2003, pp. 495-506.

Aoki et al., "*One-Pot Synthesis of Phenol and Cyclohexanone From Cycloheylbenzene Catalyzed by N-Hydroxyphthalimide(NHPI)*", Tetrahedron, 2005, vol. 61, pp. 5219-5222.

Cole et al., "*Novel Bronsted Acidic Ionic Liquids and Their Use as Dual Solvent-Catalysts*", Journal of the American Chemical Society, 2002, vol. 124, pp. 5962-5963.

Ishii et al., "*Recent Progress in Aerobic Oxidation of Hydrocarbons by N-Hydroxyimides*", Catalysis Today, 2006, vol. 117, pp. 105-113.

Knifton et al., "*Phenol/Acetone Cogeneration Via Solid Acid Catalysis*", Applied Catalysis A: General, 1997, vol. 161, pp. 199-211.

Koltunov et al., "*Efficient Cleavage of Cumene Hydroperoxide over HUSY Zeolites: The Role of Bronsted Acidity*", Applied Catalysis A: General, 2008, vol. 336, pp. 29-34.

Leng et al., "*Heteropolyanion-Based Ionic Liquids: Reaction-Induced Self-Separation Catalysts from Esterification*", Angew. Chem. Int. Ed., 2009, vol. 48, pp. 168-171.

Maksimov et al., "*$WO_3/MO_2$ (M=Zr, Sn, Ti) Heterogeneous Acid Catalysts: Synthesis, Study, and Use in Cumene Hydroperoxide Decomposition*", Kinetics and Catalysis, 2006, vol. 47, No. 4, pp. 564-571.

Meier et al., Atlas of Zeolites Structure Types, 2001 (Abstract Only).

Schmidt et al., "*New Developments in the Sunoco/UOP Phenol Technology*", presented at the AICHE Spring Meeting, Apr. 2004, New Orleans, LA.

Selvin et al., "*Catalytic Decomposition of Cumene Hydroperoxide into Phenol and Acetone*", Applied Catalysis A: General, 2001, vol. 219, pp. 125-129.

Zakoshansky, "*Acid-catalytic Cumene Hydroperoxide Cleavage Process in Boiling Acetone Medium*", presented at the AICHE Spring Meeting, Mar. 2002, New Orleans, LA.

\* cited by examiner

MIXED METAL OXIDE CATALYSTS AND USE THEREOF

PRIORITY CLAIM TO RELATED APPLICATIONS

This application is a National Stage Application of International Application No. PCT/US2012/052878 filed Aug. 29, 2012, which claims priority to U.S. Provisional Application Ser. No. 61/544,341 filed Oct. 7, 2011, the disclosures of which are fully incorporated herein by their reference.

FIELD

The present invention relates to mixed metal oxide catalysts and their use in the selective decomposition of organic oxygenate species, such as alkylaromatic hydroperoxides and dialkyl ethers.

BACKGROUND

Phenol is an important product in the chemical industry, with utility in, for example, the production of phenolic resins, bisphenol A, ε-caprolactam, adipic acid, alkyl phenols, and plasticizers. Phenol is currently produced by the selective catalytic decomposition of cumene hydroperoxide although other alkylaromatic hydroperoxides, particularly cyclohexylbenzene hydroperoxide and sec-butylbenzene hydroperoxide, are attractive precursors in the production of phenol.

Current commercial processes for the cleavage of alkylaromatic hydroperoxides almost exclusively use sulfuric acid as the catalyst, even though this yields phenol selectivities of only 92% to 96% of the theoretical yield. In addition, of course, there are many disadvantages inherent in the use of sulfuric acid. Thus, sulfuric acid is corrosive, especially in the presence of water, potentially requiring expensive material for reactor construction. In addition, sulfuric acid needs to be neutralized before product separation, which involves the use of additional chemicals, such as phenates, caustic, and/or organic amines. Moreover, the salts generated by the neutralization require separation and disposal and generate waste water which needs to be treated. There is therefore significant incentive to replace sulfuric acid with a solid acid catalyst that can alleviate or eliminate these problems.

For example, U.S. Pat. No. 6,297,406 discloses a process for producing phenol and acetone from cumene hydroperoxide comprising the step of contacting cumene hydroperoxide with a solid-acid catalyst comprising a mixed oxide of cerium and a Group IVB metal, such as zirconium. A similar process is disclosed in U.S. Pat. No. 6,169,215 but using a solid-acid catalyst comprising a mixed oxide of a Group IVB metal and a Group VIB metal, such as chromium, molybdenum, and tungsten.

International Publication No. WO2010/042261 discloses that other alkyl aromatic hydroperoxides, such as cyclohexylbenzene hydroperoxide and sec-butylbenzene hydroperoxide, can be cleaved to produce phenol in the presence of a catalyst comprising an oxide of at least one metal from Groups 3 to 5 and Groups 7 to 14 of the Periodic Table of the Elements and an oxide of at least one metal from Group 6 of the Periodic Table of the Elements. Generally, the catalyst comprises an oxide of at least one metal from Group 4 of the Periodic Table of the Elements, such as zirconia, and an oxide of at least one metal from Group 6 of the Periodic Table of the Elements, such as an oxide of molybdenum and/or tungsten. In one embodiment, the catalyst further comprises an oxide of at least one metal from Groups 8 to 11 of the Periodic Table of the Elements, such as an oxide of iron and/or copper.

The conversion of dialkyl ethers to their corresponding alkenes and alkanols is also an important reaction in a number of commercial processes. Thus, for example, this reaction is used to remove ethers, such as isopropyl ether, produced as the by-products of other processes, such as the hydration of propylene to produce isopropanol. In addition, an important route for the production of tertiary olefins involves reaction of mixed olefins with an alcohol over an acid catalyst to selectively produce a tertiary alkyl ether, separation of the ether from the remaining olefin stream, and decomposition of the ether to the desired tertiary olefin. This latter process relies on the fact that tertiary olefins react with alcohols more rapidly than either secondary or primary olefins and hence provides an effective method for extracting tertiary olefins, such as isobutene and isoamylene, from a mixed olefin stream. For the purposes of this invention, a tertiary olefin or isoolefin will be understood to be an olefin containing at least one carbon atom that is covalently bonded to three other carbon atoms.

Current commercial processes for the selective decomposition of dialkyl ethers, such as methyl tert-butyl ether (MTBE), frequently employ a fluoride-treated clay, such as hydrofluoric acid (HF) treated attapulgite (HFA), as the catalyst. However, the relatively high operating temperatures required by the HFA catalyst tends to increase the concentration of impurities such as dimethyl ether (DME) and isobutane in the product, as well as promoting side reactions, for example, diisobutylene dehydrocyclization and isobutene oligomerization and polymerization, that lead to fouling of the catalyst. As a result, the cycle length of the HFA catalyst normally ranges from only a few weeks to 30 or more days, which is a major disadvantage in that the loss of catalyst activity results in considerable losses in production time and leads to high catalyst replacement and disposal costs. There is therefore significant interest in finding alternative catalysts for the selective decomposition of ethers.

For example, U.S. Pat. No. 7,102,037 discloses a process for selectively converting a dialkyl ether to the corresponding alkene and alkanol, the process comprising contacting a feed containing at least one dialkyl ether with a catalyst comprising an acidic mixed metal oxide having the following composition:

$$X_m Y_n Z_p O_q$$

where X is at least one metal selected from Group 4 of the Periodic Table of Elements, such as zirconium, Y is at least one metal selected from Group 3 (including the Lanthanides and Actinides) and Group 6 of the Periodic Table of Elements, such as chromium, molybdenum, or tungsten, and Z is at least one metal selected from Groups 7, 8, and 11 of the Periodic Table of Elements, such as iron, manganese, or copper; m, n, p, and q are the atomic ratios of their respective components and, when m is 1, n is from about 0.01 to about 0.75, p is from 0 to about 0.1, and q is the number of oxygen atoms necessary to satisfy the valence of the other components.

According to the present invention, it has now been found that a ternary metal oxide system based on metals of Groups 3, 4, and 6 of the Periodic Table provides a solid acid catalyst in which the acid site density and strength can be tuned by control of the composition and synthesis conditions of the catalyst. The resulting catalyst can be tuned to be both active and selective for the decomposition of organic oxygenates, such as alkylaromatic hydroperoxides and dialkyl ethers.

SUMMARY

In one aspect, the invention resides in a process for the selective decomposition of an organic oxygenate, the process comprising:

contacting a feed comprising an organic oxygenate with a catalyst comprising:

(a) at least 0.1 wt % of an oxide of an element selected from Group 3 of the Periodic Table of Elements, wherein Group 3 includes the Lanthanide series;

(b) at least 0.1 wt % of an oxide of an element selected from Group 6 of the Periodic Table of Elements; and (c) at least 0.1 wt % of an oxide of at least one element selected from Group 4 of the Periodic Table of Elements, wherein the wt % s are based upon the total combined weight of the oxides in (a) through (c) and excludes any other components.

Conveniently, the catalyst comprises 0.1 wt % to 30 wt % of the oxide of an element selected from Group 3 of the Periodic Table of Elements including the Lanthanide series and/or 0.1 wt % to 30 wt % of the oxide of the element selected from Group 6 of the Periodic Table of Elements, wherein the wt % s are based upon the total combined weight of the oxides in (a) through (c) and excludes any other components.

In one embodiment, the organic oxygenate is an alkyl aromatic hydroperoxide selected from cumene hydroperoxide, cyclohexylbenzene hydroperoxide, and sec-butylbenzene hydroperoxide.

In yet another aspect, the invention resides in a process for producing phenol, the process comprising:

(i) hydroalkylating benzene with hydrogen in the presence of a hydroalkylation catalyst under conditions effective to produce a hydroalkylation reaction product comprising cyclohexylbenzene;

(ii) contacting at least a portion of the cyclohexylbenzene with oxygen in the presence of an oxidation catalyst under oxidation conditions effective to produce an oxidation product comprising cyclohexylbenzene hydroperoxide; and (iii) contacting at least a portion of the cyclohexylbenzene hydroperoxide with a cleavage catalyst under conditions to convert said cyclohexylbenzene hydroperoxide to phenol and cyclohexanone, wherein the cleavage catalyst comprises:

(a) at least 0.1 wt % of an oxide of an element selected from Group 3 of the Periodic Table of Elements, wherein Group 3 includes the Lanthanide series;

(b) at least 0.1 wt % of an oxide of an element selected from Group 6 of the Periodic Table of Elements; and (c) at least 0.1 wt % of an oxide of at least one element selected from Group 4 of the Periodic Table of Elements, wherein the wt % s are based upon the total combined weight of the oxides in (a) through (c) and excludes any other components.

Conveniently, the oxide of the element selected from Group 3 of the Periodic Table of Elements is cerium oxide or lanthanum oxide and is present in an amount of from 1 wt % to 20 wt %.

Conveniently, the oxide of the element selected from Group 6 of the Periodic Table of Elements is tungsten oxide or molybdenum oxide.

Conveniently, the oxide of at least one element selected from Group 4 of the Periodic Table of Elements is zirconium oxide.

In one embodiment, the weight ratio of the oxide of an element selected from Group 3 of the Periodic Table of Elements to the oxide of an element selected from Group 6 of the Periodic Table of Elements is from 1:1 to 1:8.

In yet a further aspect, the invention resides in a mixed metal oxide catalyst composition comprising:

(a) at least 0.1 wt % of an oxide of an element selected from Group 3 of the Periodic Table of Elements, wherein Group 3 includes the Lanthanide series;

(b) at least 0.1 wt % of an oxide of an element selected from Group 6 of the Periodic Table of Elements; and (c) at least 0.1 wt % of an oxide of at least one element selected from Group 4 of the Periodic Table of Elements, wherein the wt % s are based upon the total combined weight of the oxides in (a) through (c) and excludes any other components.

DRAWINGS

DETAILED DESCRIPTION

Figure 1:
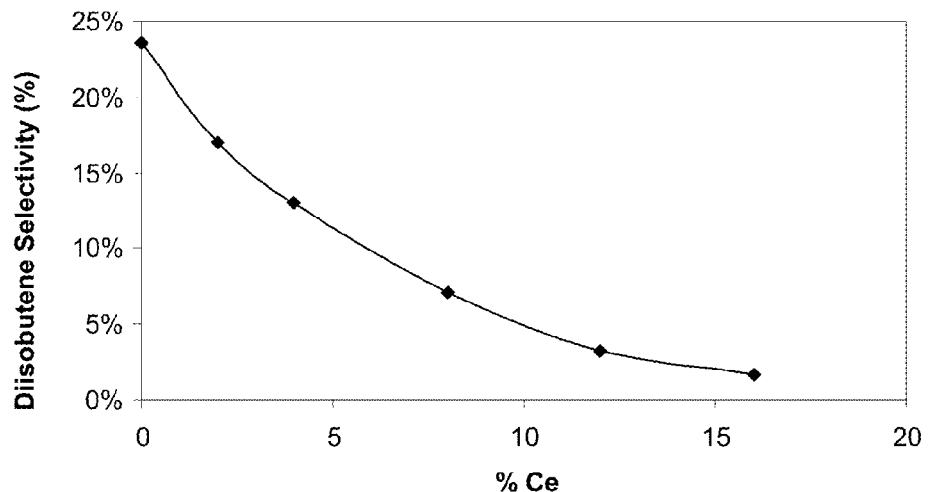
FIG. 1 is a graph of diisobutene selectivity against cerium content in the conversion of MTBE using the W/ZrO$_2$ catalyst (zero cerium) of Example 1 and the Ce/W/ZrO$_2$ catalysts of Examples 2 to 6.

Described herein is a mixed metal oxide composition, and preferably a ternary mixed metal oxide composition, and its use in the selective decomposition of an organic oxygenates, particularly dialkyl ethers and alkylaromatic hydroperoxides.

Mixed Metal Oxide Composition

The present mixed metal oxide composition comprises 0.1 wt % to 30 wt % of an oxide of an element selected from Group 3 of the Periodic Table of Elements, wherein Group 3 includes the Lanthanide series of elements; 0.1 wt % to 30 wt % of an oxide of an element selected from Group 6 of the Periodic Table of Elements; and an oxide of at least one element selected from Group 4 of the Periodic Table of Elements, wherein the percentages are based upon the total combined weight of the Group 3 oxide, the Group 6 oxide, and the Group 4 oxide, excluding any other components. Where the metal oxide composition is a ternary composition, the Group 4 metal oxide makes up the balance of the composition, namely other than the Group 3 and 6 metal oxides, and comprises 40 wt % to 99.8 wt % of the total weight of the composition.

It will be understood that the oxides described herein may be in any oxidation state. For example, the Group 6 oxide may be WO$_x$ where x can be 0, 1, 2, 3 or factions thereof depending on the process conditions. In various embodiments, one or more of the oxides are in their highest stable state.

Conveniently, the catalyst further comprises a support, such as silica, alumina, zirconia, titania, clay, carbon, and mixtures thereof As used herein, the numbering scheme for the Periodic Table Groups is used as in Richard J. Lewis Sr., HAWLEY'S CONDENSED CHEMICAL DICTIONARY (14th ed., John Wiley & Sons, Inc. 2001).

Generally, the oxide of the element selected from Group 3 of the Periodic Table of Elements is selected from cerium oxide or lanthanum oxide and is present in an amount of from 1 wt % to 20 wt % of the total weight of the composition.

Generally, the oxide of the element selected from Group 6 of the Periodic Table of Elements is selected from tungsten oxide or molybdenum oxide. Typically, the Group 6 metal oxide is present in an amount such that the weight ratio of the Group 3 metal oxide to the Group 6 metal oxide is from 1:1 to 1:8.

Conveniently, the oxide of at least one element selected from Group 4 of the Periodic Table of Elements is zirconium oxide.

Preparation of Mixed Metal Oxide Composition

In one embodiment, the mixed metal oxide catalyst composition may be prepared by impregnation, for example by impregnation of a hydrothermally treated hydrated oxide of the Group 4 metal with a single aqueous solution containing a source of ions of a Group 3 and a Group 6 metal. Alternatively, the hydrated oxide of the Group 4 metal can be impregnated with separate solutions containing the Group 3 and Group 6 metal ions, respectively. After drying, the resulting catalyst precursor is then calcined in the manner described below.

Suitable sources of ions of the Group 3 and Group 6 metals include compounds such as oxychlorides, chlorides, alkoxides, sulfates, and nitrates.

In such an embodiment, a preferred source of the Group 4 metal oxide is hydrated zirconia. The expression, hydrated zirconia, is intended to connote a material comprising zirconium atoms covalently linked to other zirconium atoms via bridging oxygen atoms and further comprising available surface hydroxyl groups. Without being limited to any particular theory, the available surface hydroxyl groups are believed to react with the Group 3 and Group 6 species to form the present acidic catalyst component. Hydrated zirconia can be formed by precalcination of $Zr(OH)_4$ at a temperature of about 100° C. to about 400° C.

Preferably, the hydrated Group 4 metal oxide, such as hydrated zirconia, is subjected to an initial hydrothermal treatment to promote the interaction with the Group 3 and Group 6 metal species. The hydrothermal treatment conditions may include a temperature of at least 80° C. or at least 100° C. The hydrothermal treatment may take place in a sealed vessel at greater than atmospheric pressure. However, a preferred mode of treatment involves the use of an open vessel under reflux conditions. Agitation of hydrated Group 4 metal oxide in the liquid medium, e.g., by the action of refluxing liquid and/or stirring, promotes the effective interaction of the hydrated oxide with the liquid medium. The duration of the contact of the hydrated oxide with the liquid medium may be at least 1 hour, or at least 8 hours. The liquid medium for this treatment may have a pH of about 7 or greater, or 9 or greater. Suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines In another, more preferred embodiment, the mixed metal oxide catalyst is prepared by co-precipitation from a liquid mixture containing a source of Group 3 metal ions and a source of Group 4 metal ions and a source of a Group 6 metal ions followed by calcination of the resulting catalyst precursor in the manner described below. The liquid mixture can be prepared by combining a first liquid solution comprising a source of one of the required metal ions with a second liquid solution comprising sources of the other two metal ions, wherein the combination takes place under conditions sufficient to cause co-precipitation of the catalyst precursor as a solid from the liquid medium. Alternatively, the source of the Group 3 metal ions may be dissolved in a first solution, the source of the Group 4 metal ions may be dissolved in a second solution and the source of Group 6 metal ions dissolved in a third solution. The three solutions can then be combined under conditions sufficient to cause co-precipitation of the catalyst precursor as a solid from the liquid mixture. As a further alternative, the source of the Group 3 metal ions, the source of the Group 4 metal ions, and the source of Group 6 metal ions may be dissolved into a single solution. This solution may then be subjected to conditions sufficient to cause co-precipitation of the catalyst, such as by the addition of a precipitating reagent to the solution. Water is a preferred solvent for these solutions.

Conveniently, the precipitation is conducted at a pH above 7. For example, the precipitating agent may be a base such as sodium hydroxide or ammonium hydroxide. The temperature at which the liquid medium is maintained during the precipitation is generally less than about 200° C., such as in the range of from about 0° C. to about 200° C. A particular range of temperatures for precipitation is from about 20° C. to about 100° C. The resulting gel may be hydrothermally treated at temperatures of at least 80° C., preferably at least 100° C. The hydrothermal treatment typically takes place in a vessel at atmospheric pressure. The gel, in one embodiment, is hydrothermally treated for up to 10 days, or up to 5 days, or up to 3 days.

The hydrated precursor to the mixed metal oxide is then recovered, for example by filtration or centrifugation, and washed and dried. The resulting material can then be calcined, such as in an oxidizing atmosphere, at a temperature of at least 400° C., or at least 500° C., for example from about 600° C. to about 900° C., and particularly from about 650° C. to about 800° C., to form the mixed metal oxide catalyst. The calcination time is typically up to 48 hours, such as for about 0.5 to about 24 hours, for example for about 1.0 to about 10 hours. In one embodiment, calcination is carried out at about 700° C. for about 1 to about 3 hours.

Uses of Mixed Metal Oxide Composition.

The resultant mixed metal oxide composition is useful as a catalyst in the selective decomposition of organic oxygenates, particularly dialkyl ethers and alkylaromatic hydroperoxides.

Thus, in one embodiment, the mixed metal oxide composition is used to decompose a dialkylether into an alcohol and an olefin. Suitable ethers for use in the process include those having the formula:

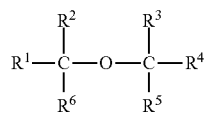

wherein $R^1$, $R^2$, $R^3$, $R^4$, $R^5$ and $R^6$ are the same or different and are selected from hydrogen, alkyl, arylalkyl and alkylaryl species, each preferably having up to 20 carbon atoms.

In general, the conditions employed are not narrowly defined and depend not only on the ether starting material but also on the desired conversion rate and product selectivity. Typically, however, the conditions will include a temperature of about 50° C. to about 320° C., a pressure of about 0 kPa to about 3500 kPa, and a weight hourly space velocity (WHSV) of about 0.1 $hr^{-1}$ to about 25 $hr^{-1}$; such as a temperature of about 100° C. to about 275° C., a pressure of about 0 kPa to about 2400 kPa and a weight hourly space velocity (WHSV) of about 0.5 hr$^1$ to about 10 hr$^{-1}$.

In one practical embodiment, the ether employed is methyl tert-butyl ether (MTBE) and the present catalyst is used to selectively decompose the MTBE to iso-butene and methanol. In another embodiment, the ether is tert-amyl methyl ether (TAME) and is selective converted to isoamylene and methanol. In these embodiments, suitable ether decomposition conditions include a temperature of about 100° C. to about 200° C., a pressure of about 0 kPa to about 1000 kPa and a weight hourly space velocity (WHSV) of about 1 hr$^1$ to about 10 hr$^{-1}$.

In another practical embodiment, the ether employed is isopropyl ether (IPE) and the present catalyst is used to selectively decompose the IPE to ispropanol and propylene. Suitable conditions for this reaction include a temperature of about 100° C. to about 320° C.; a pressure of about 100 kPa to about 3550 kPa and a weight hourly space velocity (WHSV) of about 0.5 hr$^{-1}$ to about 10 hr$^{-1}$. Conveniently, the feed to the catalyst includes water in addition to the IPE, with the molar ratio of water to IPE typically ranging from 0 to 3.

The present catalyst is also effective to selectively convert sec-butyl ether (SBE) to sec-butanol and 2-butene. In this embodiment, preferred ether decomposition conditions include a temperature of about 150° C. to about 275° C., a pressure of about 0 kPa to about 700 kPa, and a weight hourly space velocity (WHSV) of about 0.5 hr$^{-1}$ to about 10 hr$^{-1}$. Again, the feed to the catalyst conveniently includes water in addition to the SBE, with the molar ratio of water to SBE typically ranging from 0 to 3.

The present mixed metal oxide catalyst composition is also effective to convert alkylaromatic hydroperoxides to phenols. Suitable alkylaromatic hydroperoxides have the general formula (I):

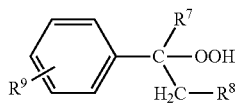

in which $R^7$ and $R^8$ each independently represents hydrogen or an alkyl group having from 1 to 4 carbon atoms, provided that $R^7$ and $R^8$ may be joined to form a cyclic group having from 4 to 10 carbon atoms, said cyclic group being optionally substituted, and $R^9$ represents hydrogen, one or more alkyl groups having from 1 to 4 carbon atoms or a cyclohexyl group.

Examples of suitable alkylaromatic hydroperoxides include cumene hydroperoxide, sec-butylbenzene hydroperoxide, p-methyl-sec-butylbenzene hydroperoxide, 1,4-diphenylcyclohexane hydroperoxide, sec-pentylbenzene hydroperoxide, sec-hexylbenzene hydroperoxide, cyclopentylbenzene hydroperoxide, cyclohexylbenzene hydroperoxide, and cyclooctylbenzene hydroperoxide. Preferred alkylaromatic hydroperoxides of general formula (I) include cumene hydroperoxide, sec-butylbenzene hydroperoxide, and cyclohexylbenzene hydroperoxide. The major products of the decomposition reaction of cyclohexyl-1-phenyl-1-hydroperoxide are phenol and cyclohexanone, which are present in substantially equimolar proportions and can be recovered from the effluent by any known method.

Such alkylaromatic hydroperoxides are typically produced by the catalyzed oxidation of an alkylaromatic compound having the general formula:

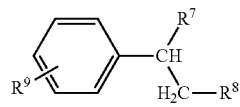

wherein $R^7$, $R^8$, and $R^9$ have the meanings ascribed in the above definition of formula (I). The alkylaromatic precursor compound is in turn produced by known aromatic alkylation processes. For example, cumene hydroperoxide is conveniently produced by oxidation of the cumene product resulting from the alkylation of benzene with propylene in presence of an MCM-22 family catalyst, such as described in U.S. Pat. No. 4,992,606. Similarly, sec-butylbenzene hydroperoxide is conveniently produced by oxidation of the sec-butylbenzene product resulting from the alkylation of benzene with linear butenes in presence of an MCM-22 family catalyst, such as described in International Patent Publication No. WO2006/015826. Cyclohexylbenzene hydroperoxide is conveniently produced by oxidation of the cyclohexylbenzene product resulting from the hydroalkylation of benzene in presence of bifunctional catalyst comprising an MCM-22 family molecular sieve and a hydrogenation metal, such as described in U.S. Pat. No. 6,037,513.

Suitable conditions for converting alkylaromatic hydroperoxides to phenols using the present mixed metal oxide catalyst include a temperature of about 20° C. to about 200° C., a pressure of about 100 kPa to about 2000 kPa, gauge, and a liquid hourly space velocity (LHSV) based on the hydroperoxide of about 1 hr$^{-1}$ to about 50 hr$^{-1}$.

The reactor used to effect the selective decomposition may be any type of reactor known to those skilled in the art. For example, the reactor may be a simple, largely open vessel operating in a near-continuous stirred tank reactor mode, or a simple, open length of pipe operating in a near-plug flow reactor mode. In one embodiment, the reactor is a fixed bed reactor. In various embodiments, the cleavage reactor comprises a plurality of reactors in series, each performing a portion of the conversion reaction, optionally operating in different modes and at different conditions selected to enhance the reaction at the pertinent conversion range. In one embodiment, the reactor is a catalytic distillation unit.

In addition to an alkylaromatic hydroperoxide, the reaction mixture contacted with the mixed metal oxide composition may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less, such as acetone, methylethyl ketone, 2- or 3-pentanone, cyclohexanone, and methylcyclopentanone.

In an embodiment in which the alkylaromatic hydroperoxide is cyclohexylbenzene hydroperoxide, the preferred polar solvent is phenol and/or cyclohexanone produced during the decomposition reaction and recycled, possibly after cooling. Generally, the polar solvent is added to the reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol. In various embodiments, the reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the reaction mixture.

In various embodiments, the reactor is operable to transport a portion of the contents through a cooling device and return the cooled portion to the reactor, thereby managing the heat of the reaction. Alternatively, the reactor may be operated adiabatically. In one embodiment, cooling coils operating within the reactor(s) remove any heat generated.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam and nylons, such as nylon 6 and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the accompanying drawings and the following Examples. Subscripts "x" and "y" denote the number of atoms of an element in a compound, which can deviate from the stoichiometric amount.

Example 1 (Comparative)

Synthesis of 16 wt % $WO_x/ZrO_2$

One hundred grams of $ZrOCl_2 \cdot 8H_2O$ were dissolved with stirring in 300 ml of distilled water. Another solution containing 10.8 grams of $(NH_4)_6H_2W_{12}O_{40} \cdot xH_2O$ in 300 ml of distilled water was prepared. The second solution was combined with the first solution with stirring. The pH of the final composite was adjusted to approximately 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A sample of this catalyst was calcined to 700° C. in flowing air for 3 hours.

Example 2

Synthesis of 2 wt % $CeO_x/16$ wt % $WO_y/ZrO_2$

One hundred grams of $ZrOCl_2 \cdot 8H_2O$ were dissolved with stirring in 300 ml of distilled water. Another solution containing 10.8 grams of $(NH_4)_6H_2W_{12}O_{40} \cdot xH_2O$ and 2.8 grams of cerium sulfate in 300 ml of distilled water was prepared. The second solution was combined with the first solution with stirring. The pH of the final composite was adjusted to approximately 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A sample of this catalyst was calcined to 700° C. in flowing air for 3 hours.

Example 3

Synthesis of 4 wt % $CeO_x/16$ wt % $WO_y/ZrO_2$

One hundred grams of $ZrOCl_2 \cdot 8H_2O$ were dissolved with stirring in 300 ml of distilled water. Another solution containing 10.8 grams of $(NH_4)_6H_2W_{12}O_{40} \cdot xH_2O$ and 5.6 grams of cerium sulfate in 300 ml of distilled water was prepared. The second solution was combined with the first solution with stirring. The pH of the final composite was adjusted to approximately 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A sample of this catalyst was calcined to 700° C. in flowing air for 3 hours.

Example 4

Synthesis of 8 wt % $CeO_x/16$ wt % $WO_y/ZrO_2$

One hundred grams of $ZrOCl_2 \cdot 8H_2O$ were dissolved with stirring in 300 ml of distilled water. Another solution containing 10.8 grams of $(NH_4)_6H_2W_{12}O_{40} \cdot xH_2O$ and 11.2 grams of cerium sulfate in 300 ml of distilled water was prepared. The second solution was combined with the first solution with stirring. The pH of the final composite was adjusted to approximately 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A sample of this catalyst was calcined to 700° C. in flowing air for 3 hours.

Example 5

Synthesis of 12 wt % $CeO_x/16$ wt % $WO_y/ZrO_2$

One hundred grams of $ZrOCl_2 \cdot 8H_2O$ were dissolved with stirring in 300 ml of distilled water. Another solution containing 10.8 grams of $(NH_4)_6H_2W_{12}O_{40} \cdot xH_2O$ and 16.8 grams of cerium sulfate in 300 ml of distilled water was prepared. The second solution was combined with the first solution with stirring. The pH of the final composite was adjusted to approximately 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A sample of this catalyst was calcined to 700° C. in flowing air for 3 hours.

Example 6

Synthesis of 16 wt % $CeO_x/16$ wt % $WO_y/ZrO_2$

One hundred grams of $ZrOCl_2 \cdot 8H_2O$ were dissolved with stirring in 300 ml of distilled water. Another solution containing 10.8 grams of $(NH_4)_6H_2W_{12}O_{40} \cdot xH_2O$ and 22.4 grams of cerium sulfate in 300 ml of distilled water was prepared. The second solution was combined with the first solution with stirring. The pH of the final composite was adjusted to approximately 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A sample of this catalyst was calcined to 700° C. in flowing air for 3 hours.

Example 7

MTBE Decomposition

The decomposition of MTBE was investigated in a fixed-bed microreactor in six separate experiments using each of the catalysts of Examples 1 through 6. Two grams of each catalyst were loaded into a ⅜" O.D. stainless steel reactor and dried with $N_2$ at 150° C. Anhydrous MTBE (99.8%, Aldrich) was fed to the reactor at 170° C., 105 psig (825 kPa), and a WHSV=5 hr$^{-1}$. Products were analyzed by on-line Gas Chromatography (GC). Table 1 summarizes the conversion of MTBE, and the isobutene, diisobutene, and methanol selectivities as a function of the cerium content of the catalyst.

TABLE 1

|  | 0% Ce | 2% Ce | 4% Ce | 8% Ce | 12% Ce | 16% Ce |
|---|---|---|---|---|---|---|
| MTBE Conversion | 90.6% | 89.1% | 87.0% | 85.3% | 84.5% | 83.7% |
| Isobutene Selectivity | 56.9% | 71.8% | 81.6% | 91.4% | 96.3% | 98.2% |
| Diisobutene Selectivity | 23.6% | 17.0% | 13.0% | 7.1% | 3.2% | 1.6% |
| Methanol Selectivity | 81.9% | 87.0% | 90.4% | 92.7% | 95.7% | 97.6% |

Figure 2:
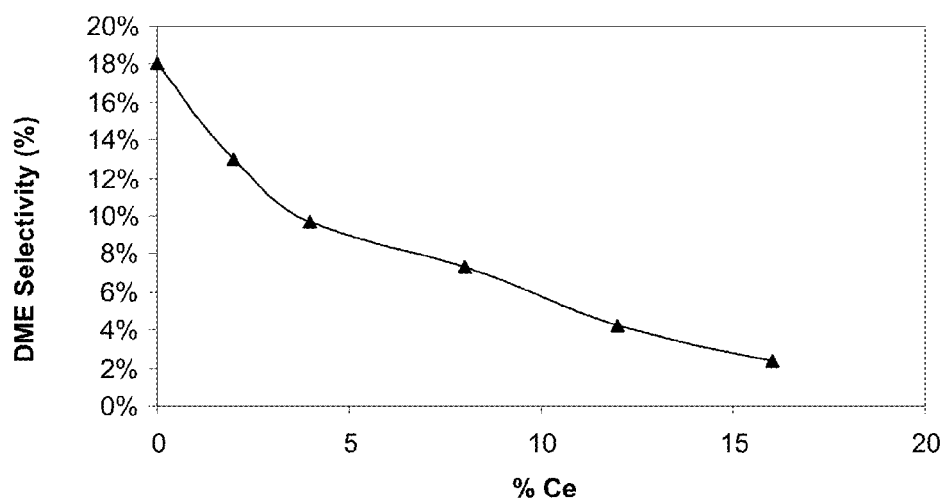
FIG. 2 is a graph of dimethyl ether selectivity against cerium content in the conversion of MTBE using the W/ZrO$_2$ catalyst (zero cerium) of Example 1 and the Ce/W/ZrO$_2$ catalysts of Examples 2 to 6.

The desired products from this reaction are isobutene and methanol. Excess acidity of the catalyst will catalyze secondary reactions, such as the dimerization of isobutene to diisobutene, and the condensation coupling of methanol to dimethyl ether. These secondary reactions are undesired, and reduce the selectivity of the primary products. By moderating the acidity of the 16 wt % W/ZrO$_2$ catalyst with increasing amounts of cerium, the selectivity toward the undesirable secondary products decreases, as shown in FIGS. 1 and 2 for diisobutene and DME, respectively.

Example 8

Cumene Hydroperoxide (CHP) Decomposition

Each of the catalysts of Examples 1 through 6 was separately tested in the decomposition of cumene hydroperoxide according to the following procedure. To a 250-ml round bottom flask fitted with a condenser, stirrer and dropping funnel, and located in a water bath for temperature control, was charged a mixture of 100.0 g of acetone and 1.00 g of the desired catalyst. The mixture was heated to reflux (57° C.) with stirring, and 45.0 g of "80%" cumene hydroperoxide (CHP) solution (analyzed as 76.6% CHP, 9.5% cumene, 10.0% dimethylphenylcarbinol (DMPC), 3.2% acetophenone) was added dropwise at an approximate rate of 2 g/min. Following addition of the CHP solution, small samples (about 0.2 ml) of the reactant solution were withdrawn at regular intervals, filtered to remove any catalyst particles, and analyzed by GC.

Figure 3:
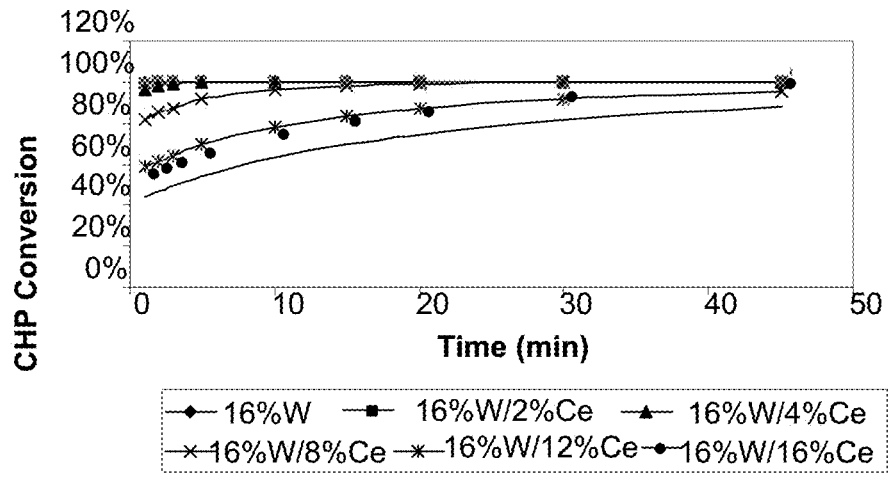
FIG. 3 is a graph of conversion of cumene hydroperoxide against reaction time for the W/ZrO$_2$ catalyst of Example 1 and the Ce/W/ZrO$_2$ catalysts of Examples 2 to 6.
Figure 4:
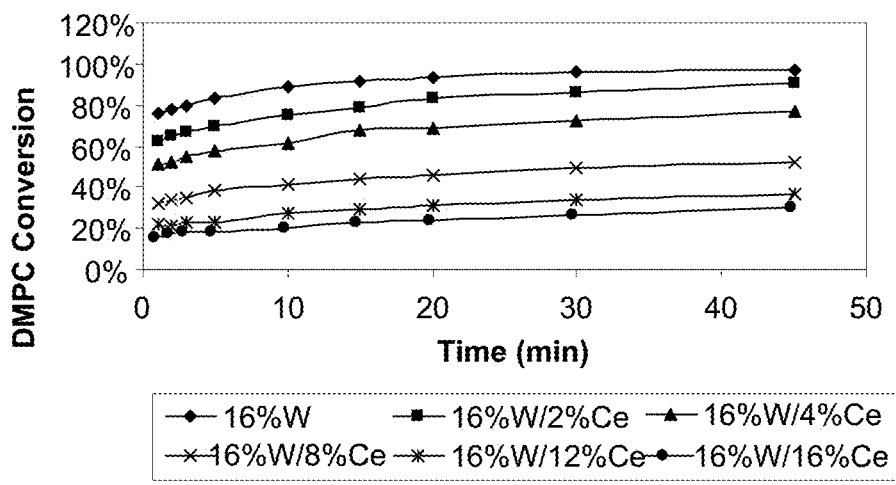
FIG. 4 is a graph of conversion of dimethylphenylcarbinol against reaction time for the W/ZrO$_2$ catalyst of Example 1 and the Ce/W/ZrO$_2$ catalysts of Examples 2 to 6.

The conversion of CHP as a function of time is shown in FIG. 3. The decomposition of CHP into phenol and acetone decreases as the acid strength of the catalyst is decreased by increasing the cerium content. This is more readily seen with some of the secondary reactions, such as the dehydration of DMPC (2-phenyl-2-propanol) into alpha-methylstyrene and water, as shown in FIG. 4.

Figure 5:
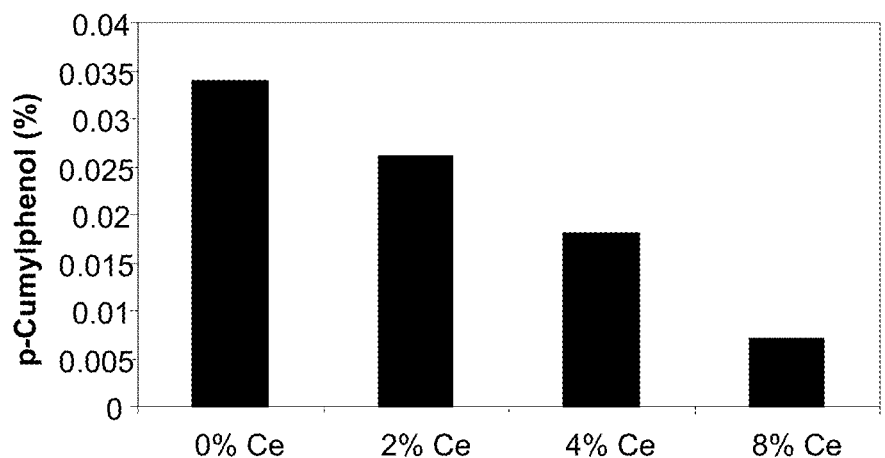
FIG. 5 is a graph of p-cumylphenol concentration after 45 minutes on stream in the conversion of cumene hydroperoxide using the W/ZrO$_2$ catalyst of Example 1 and the Ce/W/ZrO$_2$ catalysts of Examples 2 to 4.

The production of alpha-methylstyrene (AMS) via the dehydration of DMPC is not desired, since the AMS is highly reactive in the presence of acidic catalysts. One possible side reaction is the coupling of AMS and phenol leading to the formation of p-cumylphenol, an undesired byproduct. As shown in FIG. 5, the production of p-cumylphenol is reduced as the acid strength of the catalyst is decreased by increasing the cerium content.

Examples 7 and 8 serve to illustrate the concept that careful control of the acidity of the mixed metal oxide catalyst is possible by using a ternary cerium/tungsten/zirconia catalyst. It is anticipated that these catalysts would find application in other conversion reactions where careful control of acidity is desired to minimize secondary reactions. It is also anticipated that the invention of this disclosure is not limited to only cerium/tungsten/zirconia systems, but may be expanded to claim other Group 3 (including Lanthanides), Group 6 and Group 4 oxides, for example cerium/molybdenum/zirconia or lanthanum/tungsten/zirconia.

Example 9

Synthesis of W/ZrO$_2$ (~20 wt % W)

An amount of 200 grams of concentrated NH$_4$OH and 54 grams ammonium (meta)tungstate hydrate (NH$_4$)$_6$H$_2$W$_{12}$O$_{40}$.xH$_2$O were combined in 3000 ml of H$_2$O in a 4 liter beaker. The solution (A) was kept at 60° C. Separately, 500 grams of zirconyl chloride ZrOCl$_2$.xH$_2$O was dissolved in 3000 ml of H$_2$O. This solution (B) was also kept at 60° C. Solutions A and B were then combined via a nozzle mixer at a rate of 50 ml/min into a stainless steel beaker with stirring. The pH of the mixture was adjusted with concentrated NH$_4$OH to maintain a pH of 9. The resulting gel mixture was then put in a steam-box at 98° C. for 72 hours. The solid was separated by filtration and washed several times with water. The wet cake was dried in an oven at 100° C., followed by calcination in air at 800° C. for 3 hours, giving the acidic form of the material. To obtain materials with different acidity, lower calcination temperatures can be used (e.g., 600° C. or 700° C.).

Example 10

Synthesis of Ce/W/ZrO$_2$ (~1.3 wt % Ce and 20 wt % W)

An amount of 200 grams of concentrated NH$_4$OH and 54 grams ammonium (meta)tungstate hydrate (NH$_4$)$_6$H$_2$W$_{12}$O$_{40}$.xH$_2$O were combined in 3000 ml of H$_2$O in a 4 liter beaker. The solution (A) was kept at 60° C. Separately, 500 grams of zirconyl chloride ZrOCl$_2$.xH$_2$O and 10 grams cerium sulfate were dissolved in 3000 ml of H$_2$O. This solution (B) was also kept at 60° C. Solutions A and B were then combined via a nozzle mixer at a rate of 50 ml/min into a stainless steel beaker with stirring. The pH of the mixture was adjusted with concentrated NH$_4$OH to maintain a pH of 9. The resulting gel mixture was then put in a steam-box at 98° C. for 72 hours. The solid was separated by filtration and washed several times with water. The wet cake was dried in an oven at 100° C., followed by calcination in air at 650° C., 700° C., or 800° C. for 3 hours to give materials of different acidity.

Example 11

Synthesis of Ce/W/ZrO$_2$ (~2.6 wt % Ce and 20 wt % W)

The procedure of Example 10 was repeated except that 20 grams cerium sulfate was used in the preparation of solution B.

Example 12

Synthesis of Ce/W/ZrO$_2$ (~4.8 wt % Ce and 20 wt % W)

The procedure of Example 10 was repeated except that 40 grams cerium sulfate was used in the preparation of solution B.

Example 13

Cleavage of Cyclohexylbenzene Hydroperoxide (CHBHP) Using Mixed Metal Oxides in Slurry Batch Reactor An amount of 30 grams of a mixture containing CHBHP/CHB/phenol/cyclohexanone (~3/81/8/8 wt. ratio) and dodecane (internal standard) was charged to a 50-mL jacketed glass reactor with a circulating temperature bath. The bath was set to 60° C. and the reactor contents were allowed to equilibrate. Once the temperature stabilized (56° C.-57° C.), a GC sample was taken for the hot feed. The solid acid catalyst of Example 9 (2 wt % catalyst to liquid feed) was then added to the mixture. After a brief reaction exotherm, as indicated by the temperature rise inside the reactor, a 1-mL aliquot was taken at certain time intervals and the solid filtered. The liquid samples were analyzed by GC.

Figure 6:
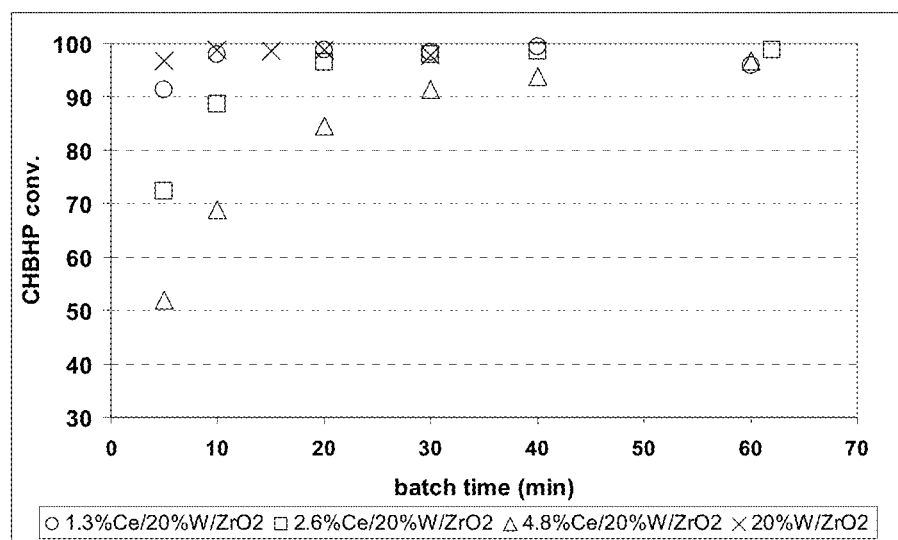
FIG. 6 is a graph of conversion of cyclohexylbenzene hydroperoxide against reaction time for the Ce/W/ZrO$_2$ catalysts of Examples 9 to 13.

The above process was repeated with each of the catalysts of Examples 10 to 12 and the results are summarized in FIG. 6 and Table 2.

FIG. 6 shows conversion of CHBHP vs. reaction time for the series of Ce/W/ZrO$_2$ catalysts containing different amounts of Ce. The activity decreases with increasing amount of Ce, consistent with the acidity being reduced with increasing amount of Ce in the mixed oxides.

Selectivities to phenol and cyclohexanone are shown in Table 2. With the exception of 1.3 wt % Ce/20 wt % W/ZrO$_2$, selectivities of the Ce/W/ZrO$_2$ series are similar while the activity decreases with increasing amount of Ce.

TABLE 2

| | Catalyst | | | |
|---|---|---|---|---|
| | 20 wt % W/ZrO$_2$ | 1.3 wt % Ce/ 20 wt % W/ZrO$_2$ | 2.6 wt % Ce/ 20 wt % W/ZrO$_2$ | 4.8 wt % Ce/ 20 wt % W/ZrO$_2$ |
| Phenol sel. (%) | 89 | 85 | 88 | 89 |
| Cyclohexanone sel. (%) | 87 | 69 | 85 | 86 |

The decrease in activity with Ce incorporation in the catalysts allows better control of the reaction rate and easier management of the reaction heat.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process comprising:
   contacting a feed comprising an organic oxygenate with a catalyst comprising:
   (a) at least 0.1 wt % of an oxide of cerium;
   (b) at least 0.1 wt % of an oxide of tungsten; and
   (c) at least 0.1 wt % of an oxide of zirconium, wherein the wt % s are based upon the total combined weight of the oxides in (a) through (c) and excludes any other components;
   wherein the organic oxygenate is an alkyl aromatic hydroperoxide or a dialkyl ether.

2. The process of claim 1, wherein the catalyst comprises 0.1 wt % to 30 wt % of the oxide of cerium, wherein the wt % is based upon the total combined weight of the oxides in (a) through (c) and excludes any other components.

3. The process of claim 1, wherein the catalyst comprises 0.1 wt % to 30 wt % of the oxide of tungsten, wherein the wt % is based upon the total combined weight of the oxides in (a) through (c) and excludes any other components.

4. The process of claim 1, wherein the organic oxygenate is an alkyl aromatic hydroperoxide.

5. The process of claim 1, wherein the organic oxygenate is selected from cumene hydroperoxide, cyclohexylbenzene hydroperoxide, and sec-butylbenzene hydroperoxide.

6. The process of claim 1, wherein the oxide of cerium is cerium dioxide.

7. The process of claim 1, wherein the oxide of cerium is present in an amount of from 1 wt % to 20 wt %.

8. The process of claim 1, wherein the oxide of tungsten is tungsten dioxide.

9. The process of claim 1, wherein the oxide of zirconium is zirconium dioxide.

10. The process of claim 1, wherein the weight ratio of the oxide of cerium to the oxide of tungsten is from 1:1 to 1:8.

11. The process of claim 1, wherein said catalyst further comprises a support that contains at least one of silica, alumina, zirconia, titania, clay, carbon, and mixtures thereof.

12. A process for producing phenol, the process comprising:
   (i) hydroalkylating benzene with hydrogen in the presence of a hydroalkylation catalyst under conditions effective to produce a hydroalkylation reaction product comprising cyclohexylbenzene;
   (ii) contacting at least a portion of the cyclohexylbenzene with an oxygen-containing compound in the presence of an oxidation catalyst under oxidation conditions effective to produce an oxidation product comprising cyclohexylbenzene hydroperoxide; and
   (iii) contacting at least a portion of the cyclohexylbenzene hydroperoxide with a cleavage catalyst under conditions to convert said cyclohexylbenzene hydroperoxide to phenol and cyclohexanone, wherein the cleavage catalyst comprises:
   (a) at least 0.1 wt % of an oxide of cerium;
   (b) at least 0.1 wt % of an oxide of tungsten; and
   (c) at least 0.1 wt % of an oxide of zirconium, wherein the wt % s are based upon the total combined weight of the oxides in (a) through (c) and excludes any other components.

13. The process of claim 12, wherein the oxide of cerium is cerium dioxide.

14. The process of claim 12, wherein the oxide of cerium is present in an amount of from 1 wt % to 20 wt %, wherein the wt % s are based upon the total combined weight of the oxides in (a) through (c) and excludes any other components.

15. The process of claim 12, wherein the oxide of tungsten is tungsten dioxide.

16. The process of claim 12, wherein the weight ratio of the oxide of cerium to the oxide of tungsten is from 1:1 to 1:8.

17. The process of claim 12, wherein the contacting step (iii) is conducted at temperature of about 20° C. to about 200° C. and a pressure of about 100 kPa, gauge to about 2000 kPa, gauge.

* * * * *